United States Patent
Li (10) Patent No.: US 7,498,410 B2
(45) Date of Patent: Mar. 3, 2009

(54) BIFUNCTIONAL VARIANTS OF RECOMBINANT TISSUE-TYPE PLASMINOGEN ACTIVATOR WITH PLATELET AGGREGATION INHIBITORY ACTIVITY

(75) Inventor: Shengfeng Li, Belmont, CA (US)

(73) Assignee: Humab Solutions, Inc., Foster City, CA (US)

( * ) Notice: Subject to any disclaimer, the term of this patent is extended or adjusted under 35 U.S.C. 154(b) by 275 days.

(21) Appl. No.: 11/489,008

(22) Filed: Jul. 18, 2006

(65) Prior Publication Data

US 2007/0015706 A1 Jan. 18, 2007

Related U.S. Application Data

(60) Provisional application No. 60/700,659, filed on Jul. 18, 2005.

(51) Int. Cl.
*C07K 1/00* (2006.01)

(52) U.S. Cl. ..................................... 530/350
(58) Field of Classification Search .................. 530/350
See application file for complete search history.

(56) References Cited

U.S. PATENT DOCUMENTS

| 5,246,850 A | 9/1993 | Bennett et al. |
| 5,486,602 A | 1/1996 | Sambrook et al. |
| 5,550,042 A | 8/1996 | Sambrook et al. |

OTHER PUBLICATIONS

Bennett et al., "Inhibition of fibrogen binding to stimulated human platelets by a monoclonal antibody," *Proc. Natl. Acad. Sci. USA* (1983) 80:2417-2421.
Kohnert et al., "Biochemical properties of the kringle 2 and protease domains are maintained in the refolded t-PA deletion variant BM 06.022," *Protein Engineering* (1992) 5(1):93-100.
Lapchak et al., "The Nonpeptide Glycoprotein IIb/IIIa Platelet Receptor Antagonist SM-20302 Reduces Tissue Plasminogen Activator-Induced Intracerebral Hemorrhage After Thromboembolic Stroke," *Stroke* (2002) 33:147-152.
Madison et al., "Serpin-resistant mutants of human tissue-type plasminogen activator," *Nature* (1989) 339:721-724.
Pennica et al., "Cloning and expression of human tissue-type plasminogen activator cDNA in *E. coli*," *Nature* (1983) 301:214-221.
Renatus et al., "Lysine 156 promotes the anomalous proenzyme activity of tPA: X-ray crystal structure of single-chain human tPA," *The EMBO Journal* (1997) 16(16): 4797-4805.
Ruoslahti et al., "New Perspectives in Cell Adhesion: RGD and Integrins," *Science* (1987) 238:491-497.
Smith et al., "Protein Loop Grafting to Construct a Variant of Tissue-type Plasminogen Activator That Binds Platelet Integrin $\alpha_{IIb}\beta_3$*," *J. Biol. Chem.* (1995) 270(51):30486-30490.
Yamada et al., "Integrin-Specific Tissue-Type Plasminogen Activator Engineered by Introduction of the Arg-Gly-Asp Sequence," *Biochem. Bioph. Res. Comm.* (1996) 228:306-311.

*Primary Examiner*—Maryam Monshipouri
(74) *Attorney, Agent, or Firm*—Ada O. Wong; Morgan, Lewis & Bockius LLP (57) ABSTRACT

The present invention provides improved tPA variants having significantly reduced susceptibility to inhibition and increased affinity for platelet integrin as compared with the wild-type tPA. The present invention also provides compositions comprising the tPA variants and polynucleotides, vectors, and host cells for producing the same as well as methods of using these tPA variants to treat disease conditions, e.g., thrombotic disorders.

11 Claims, 2 Drawing Sheets

BIFUNCTIONAL VARIANTS OF RECOMBINANT TISSUE-TYPE PLASMINOGEN ACTIVATOR WITH PLATELET AGGREGATION INHIBITORY ACTIVITY

This application claims priority to Provisional Application No. 60/700,659 filed Jul. 18, 2005.

FIELD OF THE INVENTION

The present invention is generally related to recombinant tissue-type plasminogen activators and methods of using same to treat thrombotic disorders.

BACKGROUND OF THE INVENTION

Tissue-type plasminogen activator (tPA) belongs to the chymotrypsin family of serine proteases and catalyzes the rate-limiting step in the endogenous fibrinolytic cascade, which converts circulating zymogen plasminogen into active plasmin. Plasmin in turn lyses fibrin by hydrolyzing peptide bonds in the triple-stranded connector rod regions. Five distinct structural domains make up the active human tPA protein. The DNA and amino acid sequences of human tPA were described by Pennica et al. (Nature 301:214-221, 1983).

tPA is synthesized as a single-chain polypeptide of approximately 72 kDa and converted into an active two-chain form by proteolytic cleavage at residues 275-276. This cleavage is accompanied by an increase in fibrinolytic activity. The two-chain form consists of: a 33 kDa light chain derived from the C-terminus with complete catalytic activity (C); and a 38 kDa heavy chain derived from the N-terminus with no catalytic activity. The N-terminal portion of the molecule contains four distinct structural domains including a fibronectin-like finger domain (F), an epidermal growth factor (EGF) homologous region, and two kringle structures (K1 and K2). The C-terminal portion contains what is known as the serine protease (SP) domain and comprises the active site for the fibrin-specific serine protease activity. tPA's role in fibrinolysis and potential as a therapeutic candidate for treating thrombotic disorders has been investigated over the years. Although administration of wild type human tPA has been the standard for treating acute myocardial infarction, a condition that kills more people worldwide than any other single disease, several factors have constrained its use as a therapeutic.

First, the activity of tPA is rapidly inhibited by the serpin plasminogen activator inhibitor type 1 (PAI-1) in vivo. Secondly, the enzyme is rapidly cleared from the circulation system and has a very short-half life. Third, platelet-rich thrombi are resistant to lysis by tPA and other fibrinolytic agents. To overcome some of these limiting factors of wild-type tPA and produce variants of tPA with better pharmacological profiles, studies of structure-function relationship of tPA have been carried out over the years. For example, domain deletion studies have implicated that kringle 2 (K2), and possibly the F domain, binds to fibrin and thereby mediate the fibrin-dependent activation of plasminogen by tPA. Deletion and mutation analysis also have demonstrated the role of structural elements located in the first three domains, i.e. F, EGF, and K1, in recognition by certain heptic receptors. Furthermore, it has been shown that the plasminogen activator inhibitor (PAI) binding site is located in the light chain at residues 296-304 of tPA. Thus, mutation in the binding site can empower the enzyme with resistance to PAI-1 (Madison et al., 1989. Nature 339, 721-724; U.S. Pat. No 5,550,042; 5,486,602).

PAI-1 is the primary inhibitor of tPA and other plasminogen activators in the blood. Under normal physiological conditions, PAI-1 limits the production of plasmin and serves to keep fibrinolysis in check. In certain pathological conditions, uncontrolled plasmin production can result in excessive degradation of fibrin and an increased risk of bleeding. During treatment of acute myocardial infarction, PAI-1 is a key culprit in diminishing the effectiveness of thrombolytic treatment by limiting the production of plasmin.

Recent attempts to improve tPA as a thrombolytic agent have focused primarily on substitution and/or deletion of some of the modules believed to be involved in tPA stability or its interaction with inhibitors such as PAI-1. Such efforts have culminated in the development of certain tPA-based therapeutics. For example, TNK-tPA is a derivative of tPA, in which a tetra-alanine substitution at amino acids 296-299 is introduced in the protease domain, thereby desensitizing the polypeptide to inhibition by PAI-1 (Paoni et al., 1993. Thromb Haemost. 70, 307-312; U.S. Pat. No. 5,246,850). TNK-tPA further contains mutations that abolish glycosylation in some sites to increase its half-life. In addition, an N-terminal truncated variant of tPA, rPA 06022, has been shown to prolong the half-life of the polypeptide (Kohnert et al., 1992. Protein Engineering 5, 93-100). Although second-generation tPA products, such as TNK-tPA (TNKase™, Tenecteplase) and rPA 06022 (Retavase®, reteplase), have overcome some of the problems set forth herein, these products, together with many other variants of tPA generated so far, do not solve an important problem: the resistance of platelet-rich thrombi to lysis, a phenomenon that often occurs in acute myocardial infarction (AMI) and other acute coronary syndromes (ACS).

In platelet-rich thrombi, the platelet aggregates are formed by the binding of either fibrinogen/fibrin or von Willebrand factor to the platelet membrane receptor, glycoprotein IIb/IIIa, the most abundant cell-surface protein in platelets. The blocking of the ligand binding function of glycoprotein IIb/IIIa has become one of the approaches used clinically to prevent platelet aggregation and thrombosis. As such, certain natural proteins, e.g. monoclonal antibodies, peptides, and small molecules against glycoprotein IIb/IIIa, have been identified that inhibit platelet aggregation by preventing the binding of fibrinogen/fibrin or von Willebrand factor to glycoprotein IIb/IIIa. One class of inhibitors includes the snake venom-derived disintegrins, a family of homologous peptides containing the (arginine-glycine-aspartate) RGD motif. These peptides have potent inhibitory effect on the binding of adhesive proteins to platelet glycoprotein IIb/IIIa, a process which is activated by many different stimuli (Ruoslahti E. and Pierschbacher M. D. 1987. Science 238, 491-497).

Fibrin binding to platelet glycoprotein IIb/IIIa receptors, followed by platelet-mediated clot retraction, creates a local area of high fibrin concentration, which limits the diffusion of fibrinolytic proteins such as tPA through the clot. Uncoupling fibrin from integrin receptors by inhibitor peptides can reduce the quantity of platelet-bound fibrin and accelerate the lysis of platelet-rich thrombus in a model system. This was further supported by clinical evidence showing that thrombolytic agents, when used in combination with abciximab (Reopro®), a therapeutic monoclonal antibody against glycoprotein IIb/IIIa that is capable of blocking platelet interactions with fibrinogen, can more effectively restore coronary flow in acute myocardial infarction.

In addition, studies have suggested that platelet activation and subsequent accumulation in microvessels are involved in the generation of infarcts and intracerebral hemorrhage (ICH), which sometimes can be caused by the administering of tPA to stroke patients. Studies using animal models have shown that platelet receptor glycoprotein IIb/IIIa inhibitor reduces the occurrence of tPA-induced intracerebral hemorrhage after thromboembolic stroke (Lapchak et al., 2002. Stroke, 33, 147-152).

Attempts have been made to generate integrin specific tPA. Smith et al. described the use of protein loop to construct variants of tPA that bind integrin receptor, in which a CDR3 region of an antibody against integrin αIIbβ3 was grafted into the EGF domain of tPA (Smith et al. 1995. J. Biol. Chem. 270: 30486-90). Yamada also attempted to tailor tPA mutants with affinity to integrin by inserting the RGD motif into either the Kringle I domain, the linker region between Kringle II and the protease domain, or the protease domain (Yamada et al., Bioch. Bioph. Res. Comm. 1996, 228, 306-331). According to Yamada, all of the tPA mutants generated (except 148RGD-tPA) were defective either in its catalytic activity or its ability to bind to integrin.

In light of the above, there remains a need in the art to provide methods and compositions useful for treating thrombotic disorders.

SUMMARY OF THE INVENTION

The present invention is based, in part, on the development of tPA variants with lowered susceptibility to inhibition and increased affinity for platelet integrin. Accordingly, the present invention provides tPA variants and methods of using same for the treatment of thrombotic disorders.

In one embodiment, the present invention provides a tissue plasminogen activator (tPA) containing a deactivated plasminogen activator inhibitor (PAI) binding site and a platelet integrin binding site, wherein the tPA has fibrinolytic activity and an affinity for platelet integrin.

In another embodiment, the present invention provides a pharmaceutical composition comprising the tPA variants of the present invention.

In yet another embodiment, the present invention provides polynucleotides, vectors, and host cells for encoding and expressing the tPA variants of the present invention.

In still another embodiment, the present invention provides a method for the treatment of thrombotic disorder. The method comprises administering to a subject in need of such treatment an effective amount of the tPA variants of the present invention.

In yet still another embodiment, the present invention provides a method for the treatment of acute myocardial infarction. The method comprises administering to a subject in need of such treatment an effective amount of the tPA variants of the present invention.

DESCRIPTION OF THE PREFERRED EMBODIMENTS

The present invention is based, in part, on the discovery that the controlled modification of tPA affords novel variants with improved pharmacokinetic properties, e.g. reduced susceptibility to its inhibitors and increased affinity for platelet integrin. Accordingly, the present invention provides tPA variants, compositions of tPA variants, and methods of using same for the treatment of disease conditions, e.g., thrombotic disorders.

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a variant" includes a plurality of such variants and reference to "the host cell" includes reference to one or more host cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Definitions

The terms "treat", "treating", "treatment" and the like are used interchangeably herein and mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed the disease such as enhancing the effect of vitamin D. "Treating" as used herein covers treating a disease in a vertebrate and particularly a mammal and most particularly a human, and includes:

(a) preventing the disease from occurring in a subject which may be predisposed to the disease but has not yet been diagnosed as having it;

(b) inhibiting the disease, i.e. arresting its development; or (c) relieving the disease, i.e. causing regression of the disease.

The term "subject" as used herein refers to an animal, particularly an animal susceptible to thrombotic disorders or acute myocardial infarction, preferably a human.

The term "effective amount" or "an amount effective to" or a "therapeutically effective amount" or any grammatically equivalent term means the amount that, when administered to an animal for treating a disease, is sufficient to effect treatment for that disease.

As used herein, "administering," means oral administration, administration as a suppository, topical contact, intravenous, intraperitoneal, intramuscular, intralesional, intranasal or subcutaneous administration, or the implantation of a slow-release device e.g., a mini-osmotic pump, to the subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The term "isolated" refers to a material that is substantially or essentially free from components, which are used to produce the material. As applied to the present invention, the term "isolated" refers to material that is substantially or essentially free from components which normally accompany the material in the mixture used to prepare the material. "Isolated" and "pure" are used interchangeably.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

According to the present invention, the tPA variant of the present invention contains a deactivated plasminogen activator inhibitor (PAI) binding site as well as a platelet integrin binding site. A deactivated PAI binding site can be any diminished or inhibited PAI binding site, e.g., any region containing amino acids involved in tPA's interaction with PAI and having a decreased binding activity with PAI. It is normally understood by one skilled in the art that the core of a PAI binding site includes an amino acid region corresponding to amino acids 296 to 304, in particular, amino acids 296-302 and amino acid 304 of the human tPA sequence.

In some embodiments of the invention, a deactivated PAI binding site of the present invention can be a PAI binding site containing one or more amino acid mutations, e.g., insertions, deletions, or substitutions. Such mutation can be a mutation of one or more amino acids, a single type mutation, or a combination of different types of mutations, e.g., amino acid insertion(s), deletion(s) or substitution(s). Amino acids can be inserted either with or without any amino acid deletions in a PAI binding site. In addition, amino acid substitutions include replacing one or more amino acids with the same or more number of amino acids. In additional embodiments of the invention, the deactivation of the PAI binding site can be achieved by blocking one or more amino acids in the PAI binding site. The mutation and blocking approaches may be employed alone or in combination to produce tPA variants with lowered susceptibility to inhibition.

In one embodiment, a deactivated PAI binding site of the present invention is a PAI binding site with an insertion, deletion, and/or substitution of at least two, three, four, five, six, or seven amino acids. In another embodiment, a deactivated PAI binding site of the present invention is a PAI binding site with a deletion of at least two, three, four, five, six or seven amino acids in a region corresponding to amino acids 296-302 of human tPA. In yet another embodiment, a deactivated PAI binding site of the present invention is a PAI binding site with at least two, three, four, five, six or seven amino acids deleted and substituted with an equal number of amino acids or more. In still another embodiment, a deactivated PAI binding site of the present invention is a PAI binding site that has been replaced, in whole or in part, with a motif capable of binding platelet integrin. In preferred embodiments of the invention, at least three, four, five, six, or seven amino acids in a PAI binding site are deleted and replaced with a binding site for platelet integrin.

According to the present invention, a binding site for platelet integrin includes a minimum number of amino acids required for the modified tPA of the present invention to bind a platelet integrin. The presence of such amino acid sequence serves to inhibit or decrease the activity, especially its ligand binding function, of the platelet membrane receptor, e.g. glycoprotein IIb/IIIa receptor. The platelet integrin binding site of the present invention can include any amino acid region from naturally existing polypeptides, monoclonal antibodies, e.g. CDR regions of monoclonal antibodies, small peptides, etc.

In one embodiment, the platelet integrin binding site of the present invention includes a region having an amino acid sequence corresponding to a sequence found in snake venom-derived disintegrins, a family of homologous peptides containing the RGD motif (amino acids Arg-Gly-Asp) (SEQ ID NO: 9). In another embodiment, the platelet integrin binding site of the present invention includes an amino acid region corresponding to a CDR region of a monoclonal antibody against the platelet membrane receptor, e.g., CDR3 region of an antibody against integrin αIIbβ3. In yet another embodiment, the platelet integrin binding site of the present invention includes an amino acid sequence selected from Arg-Gly-Asp (SEQ ID NO: 9), Lys-Gly-Asp (SEQ ID NO: 10), Gly-Arg-Gly-Asp-Trp-Pro-Gly (SEQ ID NO: 11), Gly-Lys-Gly-Asp-Trp-Pro-Gly (SEQ ID NO: 12), Gly-Arg-Gly-Asp-Trp-Arg-Asn (SEQ ID NO: 13) and Gly-Lys-Gly-Asp-Trp-Arg-Asn (SEQ ID NO: 14).

According to the present invention, the platelet integrin binding site of the present invention can reside in any region of the modified tPA, provided that the resulting modified tPA has an affinity for platelet integrin and still retains tPA activity. In preferred embodiments of the invention, the tPA variant should retain at least 20%, 30%, 40%, 50%, 60% or 70% of tPA activity, especially with respect to its catalytic conversion of plasminogen to plasmin. In one embodiment, the platelet integrin binding site of the present invention resides within the C-terminal region of tPA, e.g., the SP domain of tPA corresponding to amino acids 264 to 527 of human tPA. In another embodiment, the platelet integrin binding site of the present invention resides within the 37 insertion loop of tPA based on chymotrypsinogen numbering referenced in Ranatus et al., 1997. EMBO J. 16, 4797-4805. In yet another embodiment, the platelet integrin binding site of the present invention resides within a PAI binding site of tPA. In still another embodiment, the platelet integrin binding site of the present invention replaces, in whole or in part, a PAI binding site of tPA.

In general, the platelet integrin binding site of the present invention provides the tPA of the present invention with an affinity for platelet integrin. An affinity for platelet integrin includes any specific binding activity towards platelet integrin. Such specific binding activity can be presented in any form or manner, e.g., as a form of 1) any direct binding to platelet integrin, integrin αIIbβ3, 2) any specific inhibition, in part or whole, of the ligand binding activity of platelet integrin, or 3) any ability to compete specifically with an antibody against platelet integrin. For the purpose of increasing its affinity for platelet integrin, the modified tPA of the present invention can include one or more platelet integrin binding sites. In tPA having multiple platelet integrin binding sites, these sites can lie adjacent to each other or be distanced from one another, e.g., at the N-terminal end or C-terminal end of the modified tPA.

According to the present invention, the tPA of the present invention can include either part or substantially all of the sequence of a wild-type tPA. In one embodiment, the modified tPA of the present invention has a formula of F-X-C or F-X-C-X, wherein F contains amino acids 1-295 of human tPA or amino acids 176 to 295 of human tPA, C contains amino acids 303 to 527 of human tPA, and X contains an amino acid sequence selected from Arg-Gly-Asp (SEQ ID NO: 9), Lys-Gly-Asp (SEQ ID NO: 10), Gly-Arg-Gly-Asp-Trp-Pro-Gly (SEQ ID NO: 11), Gly-Lys-Gly-Asp-Trp-Pro-Gly (SEQ ID NO: 12), Gly-Arg-Gly-Asp-Trp-Arg-Asn (SEQ ID NO: 13) and Gly-Lys-Gly-Asp-Trp-Arg-Asn (SEQ ID NO: 14).

The tPA of the present invention can be made by any suitable means currently known or later discovered. In exemplary embodiments of the invention, the tPA variants can be made by recombinant or chemical means. For example, a polynucleotide encoding the tPA variant of the present invention can be readily obtained from the amino acid sequence of the tPA variant. Such polynucleotide can be operably linked to a promoter or included in an expression vector to be expressed in a prokaryotic or eukaryotic expression system. Those of skill in the art will recognize a number of prokaryotic or eukaryotic host cells that can be utilized to achieve the purpose of the present invention. In addition, the modified tPA of the present invention can be made as a single chain polypeptide or multi-chained polypeptide either in a single vector or a plurality of vectors. In exemplary embodiments of the invention, multi-chained variant may comprise a heavy chain (corresponding to amino acids 1-275 of human tPA) and light chain (corresponding to amino acids 276-527 of human tPA), shortened variants thereof, or alternative combinations thereof.

According to another aspect of the present invention, the modified tPA of the present invention can be provided in a composition, especially a pharmaceutical composition including one or more other non-active ingredients, e.g., ingredients that do not interfere with the function of the modified tPA. For example, the composition of the present invention can include a suitable carrier or be combined with other therapeutic agents.

As used herein, a "pharmaceutically acceptable carrier" includes any material, which when combined with the tPA variant retains the peptide's activity and is non-reactive with the subject's immune systems. Exemplary carriers include, but are not limited to, large, slowly metabolized macromolecules such as powders, encapsulated solids, proteins, polysaccharides, polylactic acids, polyglycolic acids, polymeric amino acids, amino acid copolymers, and inactive virus particles. or an aqueous carrier. In some embodiments, an aqueous carrier is used for the compositions of the present invention in oral formulations and includes, without limitation, thickening materials, humectants, water, buffering agents, abrasive polishing materials, emulsifying agents, surfactants, titanium dioxide, flavor system, sweetening agents, coloring agents, and mixtures thereof. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

According to another aspect of the present invention, the modified tPA of the present invention can be used to treat any disease condition associated with the thromolytic system, especially the vascular thrombolytic system. In general, the modified tPA can be used as a thrombolytic agent, e.g., an improved tPA thrombolytic agent to treat any condition treatable with wild-type tPA or other modified versions of tPA. In one embodiment, the modified tPA of the present invention can be used to treat any thrombotic disorders. In another embodiment, the modified tPA of the present invention can be used to treat any myocardial infarction and other thromboembolic disorders, e.g., thromboembolic stroke. In yet another embodiment, the modified tPA of the present invention can be used to treat acute coronary syndrome.

In general, the modified tPA of the present invention can be used alone or in combination with other therapeutics or treatments, either administered separately in various order or concurrently. According to the present invention, an effective amount of the composition of the present invention to be administered to a subject can be determined on a case-by-case basis. Factors to be considered usually include the total surface area to be treated, age, body weight, stage of the condition, other disease conditions, duration of the treatment, and the response to the initial treatment. For example, the effective dosage for intravenous administration ranges from 0.1 mg/kg to 2.5 mg/kg, or roughly 50,000 IU/kg to 1,250,000 IU/kg. (IU: International Units as determined by an in vitro clot lysis assay and as tested against the WHO standard).

Typically, the agents or compositions used in the present invention are prepared as a topical or an injectable, either as a liquid solution or suspension. However, solid forms suitable for solution in, or suspension in, liquid vehicles prior to injection can also be prepared. The composition can also be formulated into an enteric-coated tablet or gel capsule according to known methods in the art.

The agents or compositions of the present invention may be administered by any medically acceptable means depending on various factors, e.g. the site, type, and severity of the condition or injury being treated. Possible administration routes include injections, by parenteral routes such as intravascular, intravenous, intraepidural or others, as well as oral, nasal, ophthalmic, rectal, vaginal, topical, or pulmonary, e.g., by inhalation. The compositions may also be directly applied to tissue surfaces. Sustained release, pH dependent release, or other specific chemical or environmental condition mediated release administration is also specifically included in the invention, by such means as depot injections or erodible implants.

EXAMPLES

The following examples are intended to illustrate but not to limit the invention in any manner, shape, or form, either explicitly or implicitly. While they are typical of those that might be used, other procedures, methodologies, or techniques known to those skilled in the art may alternatively be used.

Example 1

Construction of Vectors Encoding Single-Chain tPA Variants Containing the K2C Domains A variety of vectors and clones expressing the unique features of the modified tPA of the present invention can be generated using conventional recombinant DNA techniques. By way of illustration, we have constructed pHS-tPA which expresses single chain human tPA K2C (Kringle 2 domain plus the catalytic domain; SEQ ID NO: 2). pHS-tPA was constructed from a wild-type human tPA cDNA clone obtained from Origene Technologies (Rockville, Md.). The K2C domains were then synthesized using PCR techniques known in the field. The primer pairs:

```
5noS
(GGGAATTCCATATGTCGTATCAGGGAAACAGTGAC (SEQ ID NO:15)
TGCTACTTT)
and

3tp
(CTAGCTAGCTTATCACGATCGCATGTTGTCAC)    (SEQ ID NO:16)
``` were used in the PCR amplification. The gene fragment was then cloned into the Nde I and Nhe I sites of pHS-25, an *E. coli* expression vector under the control of an inducible promoter. This plasmid included an amp marker to enable selection in *E. coli*. pHS-tPA expresses K2C domains with wild-type sequences within the SP domain.

Example 2

Design and Construction of Library Encoding Bifunctional Single-Chain tPA Variants Containing the K2C Domains with a Removable Cassettes To present the integrin inhibitor sequence in the 37 insertion loop in a stable and functional manner, it is essential to optimize the sequences surrounding the core binding motif. To achieve the diversity of the sequences and efficiency of screening, a library cassette with random sequences surrounding the core RGD were designed. First, the two restriction sites were introduced into pHS-tPA as follows:

| Primer pair |
|---|
| 5noS<br>(GGGAATTCCATATGTCGTATCAGGGAAACAGTGAC (SEQ ID NO:15)<br>TGCTACTTT)<br>and |
| H3C<br>(CAAGCTTCCATCTTTGCCGATCGATTCCTGTGCGG (SEQ ID NO:17)<br>GGGCATACTC) | was used to amplify one part of the tPA K2C using the above mentioned pHS-tPA as template and primer pair

```
ClaH
(TCGATCGGCAAAGATGGTAGCTTGCCAGGGGTGGG (SEQ ID NO:18)
AGGCGATG)
and

3tp
(CTAGCTAGCTTATCACGATCGCATGTTGTCAC)   (SEQ ID NO:16)
``` was used to amplify the second part of the K2C using plasmid pHS-tPA as a template. The above two PCR fragments were purified, mixed, and used as template in a recombinant PCR reaction using the primer pair 5noS and 3tp. The recombinant PCR fragment was then purified and digested with Nde I and Nhe I, ligated to pHS-25, then cut with Nde I and Nhe I to generate pHS-tPAd as shown in SEQ ID NO: 3).

To randomize both the N-terminal and C-terminal of the core amino acid, two oligos were synthesized,

```
40mR
(AGCTGCCATCTTTNNBNNBARGGGCGATNNBNNBG (SEQ ID NO:19)
GTGAT)
and

38mR
(CGATCACCVNNVNNATCGCCCYTVNNVNNAAAGAT (SEQ ID NO:20)
GGC),
``` and annealed. The annealed fragment was ligated to pHS-tPAd and cut with restriction enzymes Hind III and Cla I. The ligation was electroporated into a BL21 derivative *E. coli* strain, BL21d. Twenty colonies were then selected randomly and sequenced, and 95% of the clones were shown to contain the insert. The sequence representative of the library is identified herein as SEQ ID NO: 4.

After growing overnight on LB medium agar with 100 ug/mL Amp, the colonies were then induced with IPTG and transferred to circled filter. The colonies lifted on the filter were then lysed, denatured, and refolded as follows. The lysed colonies on the filter were denatured in 8M urea buffer (8 M urea, 0.1 M TRIS., 1 mM glycine, 1 mM EDTA, 10 mM DTT, 1 mM reduced glutathione (GSH), 0.1 mM oxidized glutathione (GSSH)) and refolded over a period of 48 h to 96 h by incubating in refolding buffer (50 mM Tris base, 15 mM L-Arginine, 2 mM NaEDTA, 0.1% Tween 80, 0.25 mM ox.glutathione, 1 mM red. Glutathione, protease inhibitors (urea needs to be diluted to 0.4 M, and pH gradually adjusted to 7.4 with 1 N HCl). The filter containing the refolded colonies was then incubated with glycoprotein IIb/IIIa.

Positive binders were identified by anti-beta3 antibody, and then secondary antibody conjugated with HRP, and detected with chromogenic substrate. Multiple variants of K2C with glycoprotein IIb/IIIa binding activity were identified, and representative clones were further analyzed by expression and purification of the recombinant proteins. Sequences of the cassette DNA (Hind III-Cla I) of the four representative variants, RR-tPA, KR-tPA, RP-tPA, and KP-tPA, were then determined as shown in SEQ ID NO: 5, 6, 7, and 8 respectively.

Example 3

Expression and Purification of Recombinant Proteins

*E. coli* culture BL21d containing the appropriate expression plasmid was inoculated in LB medium plus 5 mL glucose and 100 ug/mL Amp, and induced with 1 mM IPTG for 3 h. Cells were harvested, lysed, and separated into soluble and insoluble cell fractions by centrifugation. The fractions were initially assayed on SDS-PAGE and the recombinant protein was determined to be insoluble and formation of inclusion bodies observed. After careful removal of the supernatant, the pellet was resuspended and washed several times. The recombinant protein was dissolved in 8 M urea buffer (8 M urea, 0.1 M TRIS bases., 1 mM glycine, 1 mM EDTA, 10 mM DTT, 1 mM reduced glutathione (GSH), 0.1 mM oxidized glutathione (GSSH)). The denatured protein was refolded over a period of 48 h to 96 h by incubation in refolding buffer (50 mM Tris base, 15 mM L-Arginine, 2 mM NaEDTA, 0.1% Tween 80, 0.25 mM ox.glutathione, 1 mM red, Glutathione, protease inhibitors).

The refolded protein was then purified on L-lysine-Sepharose affinity column, which was washed and equilibrated in column buffer (buffer A: 50 mM Tris-HCl, pH 7.4; 2 mM EDTA; 0.1% Tween 80). After loading the sample to the column, the column was then washed with 8 column volumes of buffer A, followed by 8 volumes of buffer A containing 0.1 M NaCl. The protein was then eluted with buffer A containing 0.5 M NaCl and 0.2 M lysine.

Example 4

Figure 2:
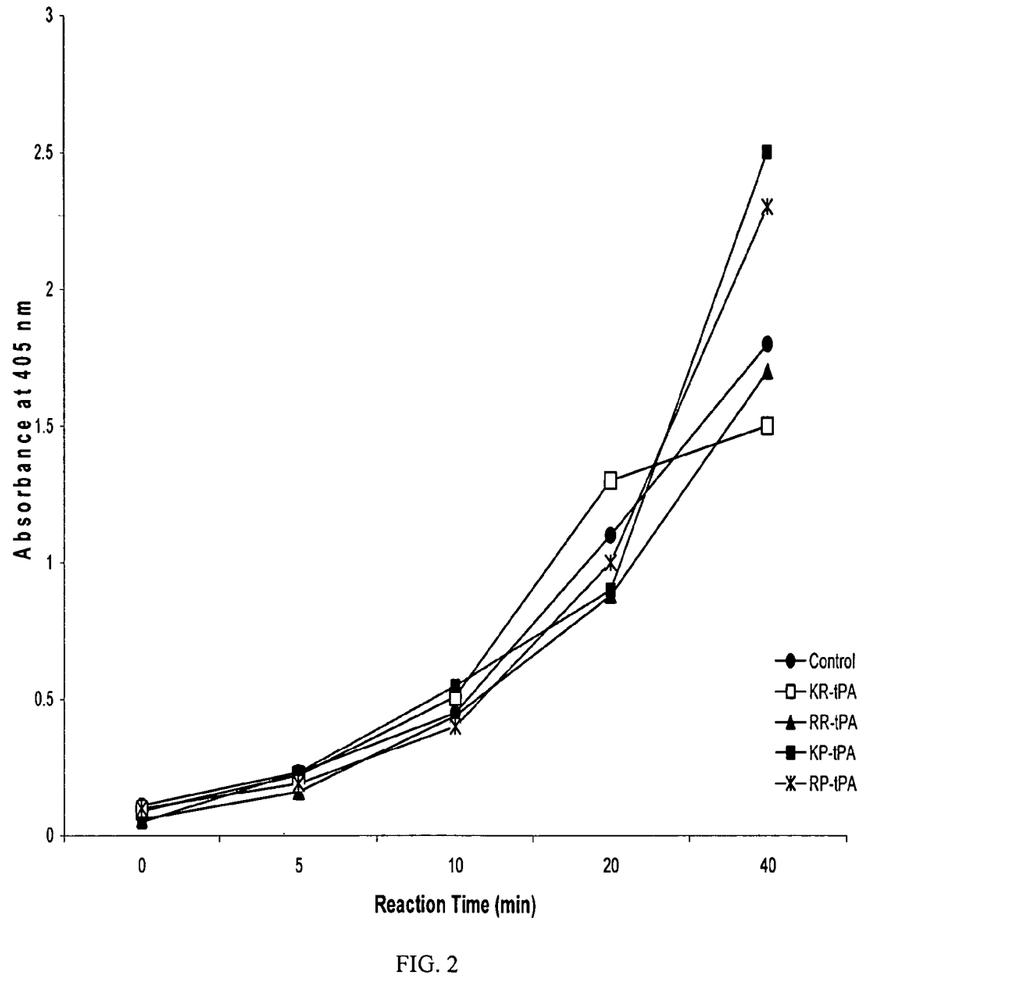
FIG. 2 shows the amidolytic activity of purified recombinant tPA variants as measured by cleavage of chromogenic peptide substrate.

Assay of Protease Catalytic Activity of Bifunctional Recombinant tPA Variants Using Chromogenic Substrate Chromogenic assays of tPA were performed using synthetic substrate H-D-isoleucyl-L-prolyl-L-arginine-p-nitroanilide-dehydrochloride (S2288, diapharma, OH). Purified recombinant tPA variants and control proteins were added to the wells of a microtiter plate with trypsin inhibitor. An aqueous solution of S-2288 was added at 2 mM in a reaction buffer containing 100 mM Tris, 100 mM NaCl, 0.02% sodium azide. Color development was monitored at 405 nm using a plate reader (Molecular Devices). The concentration of the variants was determined using anti-tPA ELISA assay. As shown in FIG. 2, the relative activity of recombinant were comparable with the control tPA, which had no insertions or mutations in the catalytic domain.

To test fibrin-mediated stimulation of the tPA variants, synthetic plasmin chromogenic substrate H-D-Val-Leu-Lys-p-nitroanilide (S-2251, diapharma, OH) was used. In this assay, plasmin-digested cyanogen bromide fragments of fibrinogen were added as a stimulator. The reaction was carried out on microtiter plate in a buffer containing 0.3 mM S-2251, 0.1 uM plasminogen, 0.2 uM cyanogens bromide and plasmin-digested fibrinogen, and 100 mM Tris-Cl, pH 7.4. Specific activity of the tPA variants was determined by comparison of activator concentration with the amount of enzyme as determined by ELISA using anti-tPA antibodies. The pharmacokinetic properties, such as fibrin binding, fibrinolysis, and fibrinogenolysis, of the tPA variants can be further characterized using methods described in the literature by a skilled artisan in the field.

Example 5

Inhibition of Fibrinogen Binding of Glycoprotein IIb/IIIa by Purified Recombinant Bifunctional tPA Variants Glycoprotein IIb/IIIa from human platelets and fibrinogen from human plasma were obtained from Calbiochem (CA). Glycoprotein IIb/IIIa complex at a concentration of 5 ug/mL was immobilized on 96-well plates in 20 mM Tris-HCl, pH 7.4, 150 mM NaCl containing 1 mM $CaCl_2$ and 1 mM $MgCl_2$. The plates were coated with integrin overnight at 4° C. Plates were then blocked by incubation with 50 mM Tris-HCl, pH 7.4, 100 mM NaCl containing 20 mg/mL bovine serum albumin. Fibrinogen with or without recombinant tPA variant protein was respectively diluted to the appropriate concentrations in binding buffer (50 mM Tris-HCl, pH 7.4, 100 mM NaCl, 0.5 mM $CaCl_2$ containing 1 mg/mL bovine serum albumin), added to integrin-immobilized microtiter wells, and allowed to bind for 2 h at 37° C.

Figure 1:
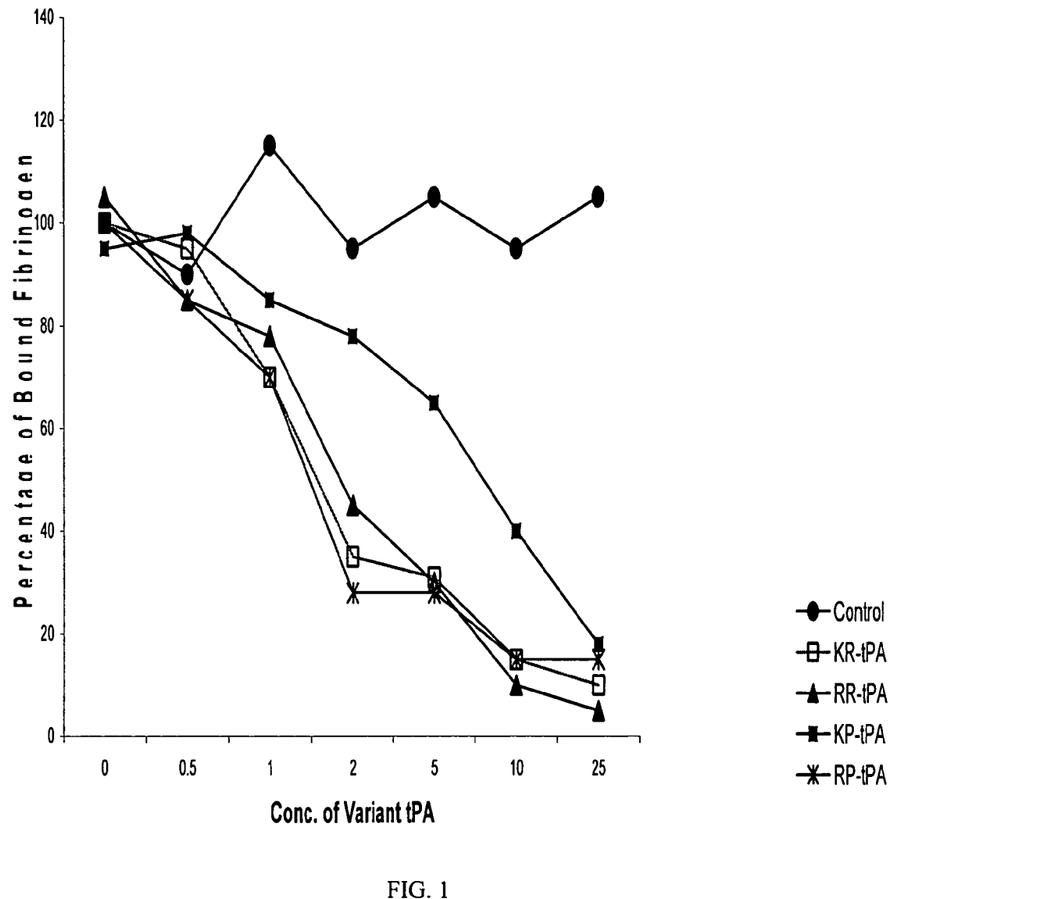
FIG. 1 shows the inhibitory effect of purified recombinant tPA variants of the present invention on fibrinogen/glycoprotein IIb/IIIa binding.

Inhibition of fibrinogen binding by the recombinant bifunctional tPA variants of the invention was determined by measuring the decrease in the amount of fibrinogen bound to the immobilized glycoprotein IIb/IIIa in the presence of either the recombinant bifunctional tPA protein or control protein. As indicated in FIG. 1, bifunctional recombinant tPA variant protein, even at nanomolar concentrations, were able to effectively abolish fibrinogen binding to immobilized glycoprotein IIb/IIIa.

Example 6

Inhibition of Platelet Aggregation by Recombinant Bifunctional tPA Variant Proteins Human gel-filtered platelets were prepared as described (Bennett et al., 1983. Proc. Natl. Aca. Sci. 80, 2417-2421). Platelet-rich plasma was isolated and chromatographed on a sephrarose column that was equilibrated with buffer containing 137 mM NaCl, 2.7 mM KCl, 10 mM Hepes, 5.6 mM glucose, 12 mM NaHCO3, and 0.3% albumin, pH 7.4. The platelets were recovered and adjusted to concentration of $2 \times 10^8$/mL in the same buffer. For the aggregation inhibition studies, 0.5 mL of platelets containing 100 ug/mL fibrinogen and 2 mM $CaCl_2$ were added to the aggregometer tube in the presence of recombinant bifunctional tPA proteins, inhibitor RGD peptide, or controls. The inhibition of aggregation was measured after the addition of ADP or thrombin by detecting changes in light transmittance using a Chronolog Aggregometer,. Results obtained therefrom demonstrate that recombinant bifunctional tPA variants effectively inhibited platelet aggregation.

Example 7

Construction of Bifunctional Variants of Other Plasminogen Activator

By analogous approaches, the plasminogen activator inhibitor (PAI) motif of other plasminogen activators, such as urokinase, can be replaced with the platelet aggregation-inhibiting sequence identified herein. Alternatively, optimal sequence with platelet aggregation inhibitory activity can be isolated in a similar method of screening, by replacing PAI sequences, in part or in whole, with a library cassette.

Example 8

Construction and Isolation of Recombinant Bifunctional tPA Variant Proteins with Thrombin Inhibitory Activities Platelet aggregation is mediated by many stimuli, one of the most potent of which is thrombin, which activates platelets through thrombin receptor-mediated signaling. An alternative approach to generating bifunctional tPA variants is to have a tPA variant that also inhibits the thrombin receptor on platelets or thrombin itself. Hirudin is one of the most potent thrombin inhibitors currently known on the market. Some amino acid sequences are known to be involved in the inhibition. A thrombin receptor-derived peptide is also known to inhibit thrombin activity. Thus, an analogous approach to producing the platelet aggregation-inhibiting tPA variants of the invention is to isolate recombinant bifunctional tPA variants, wherein the PAI sequences in the tPA catalytic domain have been partially or entirely replaced with a library cassette encoding a thrombin inhibitor peptide, e.g. hirudin.

Example 9

Design and Construction of Bifunctional Single-Chain tPA Variants Containing the K2C Domains To present an integrin inhibitor sequence in the insertion 37 loop in a stable and functional manner, it is essential to optimize the sequences surrounding the core binding motif. To that end, sequences surrounding the core RGD were designed to contain flanking cysteines capable of forming disulfide linkages. Plasmid pHS-tPAd, which was described in Example 2 (SEQ ID NO: 3), was used as vector to construct those clones. In one construct, two oligos

```
CyaRH5
(AGCTGCCATCTTTGCCTGCTATGCGCGTGGCGATT (SEQ ID NO:21)
GGCCGTGCGAG)
and

CyaRC3
(CGCTCGCACGGCCAATCGCCACGCGCATAGCAGGC (SEQ ID NO:22)
AAAGATGGC),
``` were synthesized and annealed. The annealed fragment was ligated to plasmid pHS-tPAd (SEQ ID NO: 3), and cut with restriction enzymes Hind III and Cla I. The ligation was electroporated into a BL21 derivative *E. coli* strain, BL21d. The sequence of the resulting construct pHS-tPA/CR was then determined and identified herein as SEQ ID NO: 9.

In another construct, two different oligos

```
NwkR5
(AGCTGCCATCTTTGCCTGCAACTGGAAACGTGGCG (SEQ ID NO:23)
ATTGCGAG)
and

CdgR3
(CGCTCGCAATCGCCACGTTTCCAGTTGCAGGCAAA (SEQ ID NO:24)
GATGGC),
``` were synthesized and annealed. As with the other construct, the annealed fragment was ligated to plasmid pHS-tPAd (SEQ ID NO: 3), and cut with restriction enzymes Hind III and Cla I. The ligation was electroporated into a BL21 derivative *E. coli* strain, BL21d. The sequence of the resulting construct pHS-tPA/Nwk was determined and identified herein as SEQ ID NO: 10. The recombinant protein was subsequently expressed and assayed for its pharmacokinetic properties as described in other examples.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A variant tissue plasminogen activator (tPA), as compared to SEQ ID NO: 1, wherein said variant has fibrinolytic activity and said variant comprises a deactivated plasminogen activator inhibitor (PAI) binding site and a platelet integrin binding site within the tPA serine protease domain, wherein said platelet integrin binding site has a specific binding activity for platelet integrin.

2. The variant tPA of claim 1, wherein the deactivated PAI binding site comprises a deletion of at least three amino acids within the PAI binding site of the tPA.

3. The variant tPA of claim 1, wherein the deactivated PAI binding site comprises a substitution of at least three amino acids within the PAI binding site of the tPA.

4. The variant tPA of claim 1, wherein the platelet integrin binding site resides within the PAI binding site of the tPA.

5. The variant tPA of claim 1, wherein at least three amino acids within the PAI binding site of the tPA has been replaced by a portion of the platelet integrin binding site.

6. The variant tPA of claim 1, wherein the platelet integrin binding site comprises an amino acid sequence selected from the group consisting of Arg-Gly-Asp (SEQ ID NO: 9), Lys-Gly-Asp (SEQ ID NO: 10), Gly-Arg-Gly-Asp-Trp-Pro-Gly (SEQ ID NO: 11), Gly-Lys-Gly-Asp-Trp-Pro-Gly (SEQ ID NO: 12), Gly-Arg-Gly-Asp-Trp-Arg-Asn (SEQ ID NO: 13) and Gly-Lys-Gly-Asp-Trp-Arg-Asn (SEQ ID NO: 14).

7. The variant tPA of claim 1 having a formula of F-X-C, wherein F contains amino acids 1 to 295 of human tPA, C contains amino acids 303 to 527 of human tPA, and X contains an amino acid sequence selected from the group consisting of Arg-Gly-Asp (SEQ ID NO: 9), Lys-Gly-Asp (SEQ ID NO: 10), Gly-Arg-Gly-Asp-Trp-Pro-Gly (SEQ ID NO: 11), Gly-Lys-Gly-Asp-Trp-Pro-Gly (SEQ ID NO: 12), Gly-Arg-Gly-Asp-Trp-Arg-Asn (SEQ ID NO: 13) and Gly-Lys-Gly-Asp-Trp-Arg-Asn (SEQ ID NO: 14).

8. The variant tPA of claim 7, wherein F contains amino acids 176 to 295 of human tPA.

9. The variant tPA of claim 1 having a formula of F-X-C-X, wherein F contains amino acids 1 to 295 of human tPA, C contains amino acids 303 to 527 of human tPA, and X contains an amino acid sequence selected from the group consisting of Arg-Gly-Asp (SEQ ID NO: 9), Lys-Gly-Asp (SEQ ID NO: 10), Gly-Arg-Gly-Asp-Trp-Pro-Gly (SEQ ID NO: 11), Gly-Lys-Gly-Asp-Trp-Pro-Gly (SEQ ID NO: 12), Gly-Arg-Gly-Asp-Trp-Arg-Asn (SEQ ID NO: 13) and Gly-Lys-Gly-Asp-Trp-Arg-Asn (SEQ ID NO: 14).

10. The variant tPA of claim 9, wherein F contains amino acids 176 to 295 of human tPA.

11. A composition comprising the variant tPA of claim 1 and a pharmaceutically acceptable carrier.

* * * * *

SEQUENCE LISTING

```
<160> NUMBER OF SEQ ID NOS: 24

<210> SEQ ID NO 1
<211> LENGTH: 527
<212> TYPE: PRT
<213> ORGANISM: Homo Sapiens

<400> SEQUENCE: 1

Met Tyr Gln Val Ile Cys Arg Asp Glu Lys Thr Gln Met Ile Tyr Gln
 1              5                   10                  15

Gln His Gln Ser Trp Leu Arg Pro Val Leu Arg Ser Asn Arg Val Glu
            20                  25                  30

Tyr Cys Trp Cys Asn Ser Gly Arg Ala Gln Cys His Ser Val Pro Val
        35                  40                  45

Lys Ser Cys Ser Glu Pro Arg Cys Phe Asn Gly Gly Thr Cys Gln Gln
    50                  55                  60

Ala Leu Tyr Phe Ser Asp Phe Val Cys Gln Cys Pro Glu Gly Phe Ala
65                  70                  75                  80

Gly Lys Cys Cys Glu Ile Asp Thr Arg Ala Thr Cys Tyr Glu Asp Gln
                85                  90                  95

Gly Ile Ser Tyr Arg Gly Thr Trp Ser Thr Ala Glu Ser Gly Ala Glu
            100                 105                 110

Cys Thr Asn Trp Asn Ser Ser Ala Leu Ala Gln Lys Pro Tyr Ser Gly
        115                 120                 125

Arg Arg Pro Asp Ala Ile Arg Leu Gly Leu Gly Asn His Asn Tyr Cys
    130                 135                 140

Arg Asn Pro Asp Arg Asp Ser Lys Pro Trp Cys Tyr Val Phe Lys Ala
145                 150                 155                 160
```

```
Gly Lys Tyr Ser Ser Glu Phe Cys Ser Thr Pro Ala Cys Ser Glu Gly
                165                 170                 175

Asn Ser Asp Cys Tyr Phe Gly Asn Gly Ser Ala Tyr Arg Gly Thr His
            180                 185                 190

Ser Leu Thr Glu Ser Gly Ala Ser Cys Leu Pro Trp Asn Ser Met Ile
        195                 200                 205

Leu Ile Gly Asn Val Tyr Thr Ala Gln Asn Pro Ser Ala Gln Ala Leu
    210                 215                 220

Gly Leu Gly Lys His Asn Tyr Cys Arg Asn Pro Asp Gly Asp Ala Lys
225                 230                 235                 240

Pro Trp Cys His Val Leu Lys Asn Arg Arg Leu Thr Trp Glu Tyr Cys
            245                 250                 255

Asp Val Pro Ser Cys Ser Thr Cys Gly Leu Arg Gln Tyr Ser Gln Pro
                260                 265                 270

Gln Phe Arg Ile Lys Gly Gly Leu Phe Ala Asp Ile Ala Ser His Pro
            275                 280                 285

Trp Gln Ala Ala Ile Phe Ala Lys His Arg Arg Ser Pro Gly Glu Arg
        290                 295                 300

Phe Leu Cys Gly Gly Ile Leu Ile Ser Ser Cys Trp Ile Leu Ser Ala
305                 310                 315                 320

Ala His Cys Phe Gln Glu Arg Phe Pro Pro His His Leu Thr Val Ile
            325                 330                 335

Leu Gly Arg Thr Tyr Arg Val Val Pro Gly Glu Glu Glu Gln Lys Phe
                340                 345                 350

Glu Val Glu Lys Tyr Ile Val His Lys Glu Phe Asp Asp Asp Thr Tyr
            355                 360                 365

Asp Asn Asp Ile Ala Leu Leu Gln Leu Lys Ser Asp Ser Ser Arg Cys
        370                 375                 380

Ala Gln Glu Ser Ser Val Val Arg Thr Val Cys Leu Pro Pro Ala Asp
385                 390                 395                 400

Leu Gln Leu Pro Asp Trp Thr Glu Cys Glu Leu Ser Gly Tyr Gly Lys
            405                 410                 415

His Glu Ala Leu Ser Pro Phe Tyr Ser Glu Arg Leu Lys Glu Ala His
                420                 425                 430

Val Arg Leu Tyr Pro Ser Ser Arg Cys Thr Ser Gln His Leu Leu Asn
            435                 440                 445

Arg Thr Val Thr Asp Asn Met Leu Cys Ala Gly Asp Thr Arg Ser Gly
        450                 455                 460

Gly Pro Gln Ala Asn Leu His Asp Ala Cys Gln Gly Asp Ser Gly Gly
465                 470                 475                 480

Pro Leu Val Cys Leu Asn Asp Gly Arg Met Thr Leu Val Gly Ile Ile
            485                 490                 495

Ser Trp Gly Leu Gly Cys Gly Gln Lys Asp Val Pro Gly Val Tyr Thr
                500                 505                 510

Lys Val Thr Asn Tyr Leu Asp Trp Ile Arg Asp Asn Met Arg Pro
            515                 520                 525

<210> SEQ ID NO 2
<211> LENGTH: 1071
<212> TYPE: DNA
<213> ORGANISM: Artificial Sequence
<220> FEATURE:
<223> OTHER INFORMATION: Truncated single chain tPA containing k2C,
      expressed in plasmid as pHS-tPA.
```

-continued

```
<400> SEQUENCE: 2
atgtcgtatc agggaaacag tgactgctac tttgggaatg ggtcagccta ccgtggcacg      60
cacagcctca ccgagtcggg tgcctcctgc ctcccgtgga attccatgat cctgataggc     120
aatgtttaca cagcacagaa ccccagtgcc caggcactgg gcctgggcaa acataattac     180
tgccggaatc ctgatgggga tgccaagccc tggtgccacg tgctgaagaa ccgcaggctg     240
acgtgggagt actgtgatgt gcctcctgc tccacctgcg gcctgagaca gtacagccag     300
cctcagtttc gcatcaaagg agggctcttc gccgacatcg cctcccaccc ctggcaggct     360
gccatctttg ccaagcacag gaggtcgccc ggagagcggt tcctgtgcgg ggcatactc     420 atcagctcct gctggattct ctctgccgcc cactgcttcc aggagaggtt ccgccccac     480 cacctgacgg tgatcttggg cagaacatac cgggtggtcc ctggcgagga ggagcagaaa     540
tttgaagtcg aaaaatacat tgtccataag gaattcgatg atgacactta cgacaatgac     600
attgcgctgc tgcagctgaa atcggattcg tcccgctgtg cccaggagag cagcgtggtc     660
cgcactgtgt gccttccccc ggcggacctg cagctgccgg actggacgga gtgtgagctc     720
tccggctacg gcaagcatga ggccttgtct cctttctatt cggagcggct gaaggaggct     780
catgtcagac tgtacccatc cagccgctgc acatcacaac atttacttaa cagaacagtc     840
accgacaaca tgctgtgtgc tggagacact cggagcggcg ggccccaggc aaacttgcac     900
gacgcctgcc agggcgattc ggaggccccc ctggtgtgtc tgaacgatgg ccgcatgact     960
ttggtgggca tcatcagctg gggcctgggc tgtggacaga aggatgtccc gggtgtgtac    1020
accaaggtta ccaactacct agactggatt cgtgacaaca tgcgaccgtg a             1071

<210> SEQ ID NO 3
<211> LENGTH: 1050
<212> TYPE: DNA
<213> ORGANISM: Artificial Sequence
<220> FEATURE:
<223> OTHER INFORMATION: Truncated single chain tPA containing K2C with
      sequences for Hind III -Cla I cassette for
      insertion of library oligonucleotide for
      mutagenesis.

<400> SEQUENCE: 3
atgtcgtatc agggaaacag tgactgctac tttgggaatg ggtcagccta ccgtggcacg      60
cacagcctca ccgagtcggg tgcctcctgc ctcccgtgga attccatgat cctgataggc     120
aatgtttaca cagcacagaa ccccagtgcc caggcactgg gcctgggcaa acataattac     180
tgccggaatc ctgatgggga tgccaagccc tggtgccacg tgctgaagaa ccgcaggctg     240
acgtgggagt actgtgatgt gcctcctgc tccacctgcg gcctgagaca gtacagccag     300
cctcagtttc gcatcaaagg agggctcttc gccgacatcg cctcccaccc ctggcaagct     360
tccatctttg ccgatcgatt cctgtgcggg gcatactca tcagctcctg ctggattctc     420
tctgccgccc actgcttcca ggagaggttt ccgccccacc acctgacggt gatcttgggc     480
agaacatacc gggtggtccc tggcgaggag agcagaaat ttgaagtcga aaaatacatt     540
gtccataagg aattcgatga tgacacttac gacaatgaca ttgcgctgct gcagctgaaa     600
tcggattcgt cccgctgtgc ccaggagagc agcgtggtcc gcactgtgtg ccttccccccg     660 gcggacctgc agctgccgga ctggacggag tgtgagctct ccggctacgg caagcatgag     720
gccttgtctc ctttctattc ggagcggctg aaggaggctc atgtcagact gtacccatcc     780
agccgctgca catcacaaca tttacttaac agaacagtca ccgacaacat gctgtgtgct     840
```

```
ggagacactc ggagcggcgg gccccaggca aacttgcacg acgcctgcca gggcgattcg    900
ggaggccccc tggtgtgtct gaacgatggc cgcatgactt tggtgggcat catcagctgg    960
ggcctgggct gtggacagaa ggatgtcccg ggtgtgtaca ccaaggttac caactaccta   1020
gactggattc gtgacaacat gcgaccgtga                                    1050

<210> SEQ ID NO 4
<211> LENGTH: 1071
<212> TYPE: DNA
<213> ORGANISM: Artificial Sequence
<220> FEATURE:
<223> OTHER INFORMATION: Truncated single chain tPA containing K2C with
      sequences encoding R/KGD core sequence and random
      adjacent amino acid
<220> FEATURE:
<221> NAME/KEY: misc_feature
<222> LOCATION: 370, 371, 373, 374, 385, 386, 388, 389, 391, 392
<223> OTHER INFORMATION: n = A,T,C or G

<400> SEQUENCE: 4
atgtcgtatc agggaaacag tgactgctac tttgggaatg ggtcagccta ccgtggcacg     60
cacagcctca ccgagtcggg tgcctcctgc ctcccgtgga attccatgat cctgataggc    120
aatgtttaca cagcacagaa ccccagtgcc caggcactgg gcctgggcaa acataattac    180
tgccggaatc ctgatgggga tgccaagccc tggtgccacg tgctgaagaa ccgcaggctg    240
acgtgggagt actgtgatgt gccctcctgc tccacctgcg gcctgagaca gtacagccag    300
cctcagtttc gcatcaaagg agggctcttc gccgacatcg cctcccaccc ctggcaagct    360
gccatctttn nbnnbarggg cgatnnbnnb nnbgatcgat tcctgtgcgg gggcatactc    420
atcagctcct gctggattct ctctgccgcc cactgcttcc aggagaggtt ccgccccac    480 cacctgacgg tgatcttggg cagaacatac cgggtggtcc ctggcgagga ggagcagaaa    540
tttgaagtcg aaaaatacat tgtccataag gaattcgatg atgacactta cgacaatgac    600
attgcgctgc tgcagctgaa atcggattcg tcccgctgtg cccaggagag cagcgtggtc    660
cgcactgtgt gccttccccc ggcggacctg cagctgccgg actggacgga gtgtgagctc    720
tccggctacg gcaagcatga ggccttgtct cctttctatt cggagcggct gaaggaggct    780
catgtcagac tgtacccatc cagccgctgc acatcacaac atttacttaa cagaacagtc    840
accgacaaca tgctgtgtgc tggagacact cggagcggcg ggccccaggc aaacttgcac    900
gacgcctgcc agggcgattc gggaggcccc ctggtgtgtc tgaacgatgg ccgcatgact    960
ttggtgggca tcatcagctg gggcctgggc tgtggacaga aggatgtccc gggtgtgtac   1020
accaaggtta ccaactacct agactggatt cgtgacaaca tgcgaccgtg a            1071

<210> SEQ ID NO 5
<211> LENGTH: 40
<212> TYPE: DNA
<213> ORGANISM: Artificial Sequence
<220> FEATURE:
<223> OTHER INFORMATION: Cassette DNA of RR-tPA variant.

<400> SEQUENCE: 5
agctgccatc tttgccggca ggggcgattg gcgcaatgat                            40

<210> SEQ ID NO 6
<211> LENGTH: 40
<212> TYPE: DNA
<213> ORGANISM: Artificial Sequence
<220> FEATURE:
<223> OTHER INFORMATION: Cassette DNA of KR-tPA variant.
```

```
<400> SEQUENCE: 6
agctgccatc tttgccggca agggcgattg gcgcaatgat                    40

<210> SEQ ID NO 7
<211> LENGTH: 40
<212> TYPE: DNA
<213> ORGANISM: Artificial Sequence
<220> FEATURE:
<223> OTHER INFORMATION: Cassette DNA of RP-tPA variant.

<400> SEQUENCE: 7
agctgccatc tttgccggca ggggcgattg gccgggcgat                    40

<210> SEQ ID NO 8
<211> LENGTH: 40
<212> TYPE: DNA
<213> ORGANISM: Artificial Sequence
<220> FEATURE:
<223> OTHER INFORMATION: Cassette DNA of KP-tPA variant.

<400> SEQUENCE: 8
agctgccatc tttgccggca agggcgattg gccgggcgat                    40

<210> SEQ ID NO 9
<211> LENGTH: 3
<212> TYPE: PRT
<213> ORGANISM: Artificial Sequence
<220> FEATURE:
<223> OTHER INFORMATION: portion of platelet integrin binding site

<400> SEQUENCE: 9

Arg Gly Asp
 1

<210> SEQ ID NO 10
<211> LENGTH: 3
<212> TYPE: PRT
<213> ORGANISM: Artificial Sequence
<220> FEATURE:
<223> OTHER INFORMATION: portion of platelet integrin binding site

<400> SEQUENCE: 10

Lys Gly Asp
 1

<210> SEQ ID NO 11
<211> LENGTH: 7
<212> TYPE: PRT
<213> ORGANISM: Artificial Sequence
<220> FEATURE:
<223> OTHER INFORMATION: portion of platelet integrin binding site

<400> SEQUENCE: 11

Gly Arg Gly Asp Trp Pro Gly
 1               5

<210> SEQ ID NO 12
<211> LENGTH: 7
<212> TYPE: PRT
<213> ORGANISM: Artificial Sequence
<220> FEATURE:
<223> OTHER INFORMATION: portion of platelet integrin binding site

<400> SEQUENCE: 12

Gly Lys Gly Asp Trp Pro Gly
```

<210> SEQ ID NO 13
<211> LENGTH: 7
<212> TYPE: PRT
<213> ORGANISM: Artificial Sequence
<220> FEATURE:
<223> OTHER INFORMATION: portion of platelet integrin binding site

<400> SEQUENCE: 13

Gly Arg Gly Asp Trp Arg Asn
 1               5

<210> SEQ ID NO 14
<211> LENGTH: 7
<212> TYPE: PRT
<213> ORGANISM: Artificial Sequence
<220> FEATURE:
<223> OTHER INFORMATION: portion of platelet integrin binding site

<400> SEQUENCE: 14

Gly Lys Gly Asp Trp Arg Asn
 1               5

<210> SEQ ID NO 15
<211> LENGTH: 44
<212> TYPE: DNA
<213> ORGANISM: Artificial Sequence
<220> FEATURE:
<223> OTHER INFORMATION: 5noS primer

<400> SEQUENCE: 15
gggaattcca tatgtcgtat cagggaaaca gtgactgcta cttt          44

<210> SEQ ID NO 16
<211> LENGTH: 32
<212> TYPE: DNA
<213> ORGANISM: Artificial Sequence
<220> FEATURE:
<223> OTHER INFORMATION: 3tp primer

<400> SEQUENCE: 16
ctagctagct tatcacgatc gcatgttgtc ac                       32

<210> SEQ ID NO 17
<211> LENGTH: 45
<212> TYPE: DNA
<213> ORGANISM: Artificial Sequence
<220> FEATURE:
<223> OTHER INFORMATION: H3C primer

<400> SEQUENCE: 17
caagcttcca tctttgccga tcgattcctg tgcggggca tactc           45

<210> SEQ ID NO 18
<211> LENGTH: 43
<212> TYPE: DNA
<213> ORGANISM: Artificial Sequence
<220> FEATURE:
<223> OTHER INFORMATION: ClaH primer

<400> SEQUENCE: 18
tcgatcggca aagatggtag cttgccaggg gtgggaggcg atg           43

<210> SEQ ID NO 19
<211> LENGTH: 40

```
<212> TYPE: DNA
<213> ORGANISM: Artificial Sequence
<220> FEATURE:
<223> OTHER INFORMATION: 40mR oligo
<220> FEATURE:
<221> NAME/KEY: misc_feature
<222> LOCATION: 14, 15, 17, 18, 29, 30, 32, 33
<223> OTHER INFORMATION: n = A,T,C or G

<400> SEQUENCE: 19
agctgccatc tttnnbnnba rgggcgatnn bnnbggtgat                              40

<210> SEQ ID NO 20
<211> LENGTH: 38
<212> TYPE: DNA
<213> ORGANISM: Artificial Sequence
<220> FEATURE:
<223> OTHER INFORMATION: 38mR oligo
<220> FEATURE:
<221> NAME/KEY: misc_feature
<222> LOCATION: 10, 11, 13, 14, 25, 26, 28, 29
<223> OTHER INFORMATION: n = A,T,C or G

<400> SEQUENCE: 20
cgatcaccvn nvnnatcgcc cytvnnvnna aagatggc                                38

<210> SEQ ID NO 21
<211> LENGTH: 46
<212> TYPE: DNA
<213> ORGANISM: Artificial Sequence
<220> FEATURE:
<223> OTHER INFORMATION: CyaRH5 oligo

<400> SEQUENCE: 21
agctgccatc tttgcctgct atgcgcgtgg cgattggccg tgcgag                       46

<210> SEQ ID NO 22
<211> LENGTH: 44
<212> TYPE: DNA
<213> ORGANISM: Artificial Sequence
<220> FEATURE:
<223> OTHER INFORMATION: CyaRC3 oligo

<400> SEQUENCE: 22
cgctcgcacg gccaatcgcc acgcgcatag caggcaaaga tggc                         44

<210> SEQ ID NO 23
<211> LENGTH: 43
<212> TYPE: DNA
<213> ORGANISM: Artificial Sequence
<220> FEATURE:
<223> OTHER INFORMATION: NwkR5 oligo

<400> SEQUENCE: 23
agctgccatc tttgcctgca actggaaacg tggcgattgc gag                          43

<210> SEQ ID NO 24
<211> LENGTH: 41
<212> TYPE: DNA
<213> ORGANISM: Artificial Sequence
<220> FEATURE:
<223> OTHER INFORMATION: CdgR3 oligo

<400> SEQUENCE: 24
cgctcgcaat cgccacgttt ccagttgcag gcaaagatgg c                            41
```